United States Patent [19]

Tsusaka et al.

[11] Patent Number: 5,622,617
[45] Date of Patent: Apr. 22, 1997

[54] GARBAGE TREATING APPARATUS WITH CONNECTED MOISTURE SENSOR AND CONTROLLER

[75] Inventors: Harushige Tsusaka; Tomisaburo Azuma; Susumu Kawakami; Hidehiko Kishie; Kaoru Yamashita; Hiroyasu Kawanishi; Kenji Esashi; Koichi Fujita; Yoshihide Yoshikawa; Masakatsu Nakamura; Hideki Minoura; Hideo Fujimoto; Masanori Koyamoto; Tadashi Yoshimura; Etsuko Kajita, all of Kadoma, Japan

[73] Assignee: Matsushita Electric Works, Ltd, Japan

[21] Appl. No.: 386,531

[22] Filed: Feb. 10, 1995

[30] Foreign Application Priority Data

| Feb. 15, 1994 | [JP] | Japan | 6-018479 |
| Feb. 15, 1994 | [JP] | Japan | 6-018480 |
| Feb. 18, 1994 | [JP] | Japan | 6-021177 |
| Aug. 26, 1994 | [JP] | Japan | 6-202519 |
| Dec. 22, 1994 | [JP] | Japan | 6-319657 |

[51] Int. Cl.$^6$ .............. B01D 17/12; C02F 3/02
[52] U.S. Cl. .............. 210/85; 4/111.1; 4/111.2; 4/111.5; 210/141; 210/143; 210/178; 210/614; 366/145; 422/225; 435/262.5
[58] Field of Search .......... 210/85, 96.1, 141, 210/143, 198.1, 205, 614, 173, 177, 178, 179, 180; 422/62, 105, 111; 436/39, 55; 364/496, 497, 500; 435/259, 262, 262.5; 324/696; 4/111.1, 111.5, 111.2, 111.6, DIG. 12; 71/9

[56] References Cited

U.S. PATENT DOCUMENTS

| 4,174,371 | 11/1979 | Bell et al. | 4/DIG. 12 |
| 4,532,797 | 8/1985 | Yang | 324/696 |
| 4,627,116 | 12/1986 | Shimizu | 210/173 |
| 4,663,045 | 5/1987 | Yeagley | 210/614 |
| 5,114,081 | 5/1992 | Takenaka | 210/173 |

FOREIGN PATENT DOCUMENTS

| 4216647 | 11/1993 | Germany . |
| 4334498 | 5/1994 | Germany . |
| 4301116 | 7/1994 | Germany . |
| 4318824 | 12/1994 | Germany . |
| 2/1291 | 1/1990 | Japan . |
| 2/30760 | 7/1990 | Japan . |
| 3/22385 | 5/1991 | Japan . |
| 4/10398 | 2/1992 | Japan . |
| 4-363650 | 12/1992 | Japan | 364/496 |
| 5/88683 | 12/1993 | Japan . |

*Primary Examiner*—Joseph W. Drodge
*Attorney, Agent, or Firm*—Burns, Doane, Swecker & Mathis, L.L.P.

[57] ABSTRACT

A garbage treating apparatus for highly efficient garbage treatment without loss in required energy nor requiring continuous control of the treatment is provided by constituting the apparatus for accommodating within a treating vessel a fermentative garbage decomposing agent carrying a microparasite and the garbage, and mixing them for a fermentative decomposing treatment of the garbage through one of a plurality of treating modes mutually selectably changed over in response to sensed moisture content of the resulting garbage mixture sensed by a moisture sensing mechanism.

10 Claims, 17 Drawing Sheets

$T_0$ MEASURING    $T_1$ MEASURING

GARBAGE TREATING APPARATUS WITH CONNECTED MOISTURE SENSOR AND CONTROLLER

BACKGROUND OF THE INVENTION

This invention relates to a garbage treating apparatus made for a smooth realization of fermentative decomposing treatment of garbage.

DESCRIPTION OF RELATED ART

In recent years, it has been developed to discard sewage containing organic matter and water after subjecting it to a fermentative decomposing treatment (fermentation) with microorganism utilized to an extent of causing no environmental influence, and the garbage treating apparatus has been employed in executing such treatment.

The garbage treating apparatus is constituted by a treating vessel filled with such fermentative garbage decomposing agent as wooden chips carrying a microparasite, such agent containing a microorganism as disclosed in, for example, Japanese Patent Publications No. 4-10398 and No. 2-30760 and Japanese Utility Model Publication No. 3-22385. In this case, the garbage put through an inlet port into the treating vessel is mixed with the decomposing agent carrying the microparasite while being brought into contact with air to have the garbage decomposed by means of the microparasite of the garbage treating agent, with water content evaporated simultaneously. An example of entire structure of the garbage treating apparatus of this kind has been disclosed in Japanese Utility Model Publication No. 5-88683.

In Japanese Utility Model Laid-Open Publication No. 2-1291, there has been disclosed a treating apparatus in which a rotary shaft having a stirring part is provided in the treating vessel for stirring the garbage put into the vessel.

In the foregoing garbage treating apparatus, however, operating time of the rotary shaft or a garbage discharging means is fixed irrespective of the amount of garbage thrown into the treating vessel so that, when the garbage amount becomes excessive, there arises a problem that required treating time is prolonged or the treatment is caused to become insufficient, and a sequential throwing of the garbage into the apparatus for days renders the garbage amount to be excessive enough for further increasing the required treating time. While a measure may be taken for elevating a treating capacity as a whole of the apparatus, required energy for the treatment with the apparatus is made wasteful when the amount of thrown-in garbage is less, and it often happens that the apparatus is enlarged in size so as to have manufacturing costs increased.

SUMMARY OF THE INVENTION

Accordingly, a primary object of the present invention is to provide a garbage treating apparatus which can realize a highly efficient and excellent treatment in all events of various states of garbage where the thrown-in amount of garbage is large or small, moisture or water content of the garbage is high or low, and so on.

More specifically, it is a further object of the present invention to realize a garbage treating apparatus generally improved remarkably in the treating efficiency with such arrangement that, for example, an operational mode once set for a decomposition treatment of a larger amount of garbage can be automatically changed over to an ordinary treating mode after a passage of a predetermined time so as to be able to prevent required treating energy from being lost when an excessively dried state of the garbage is reached in a period of several days for which the user is absent, that the user can be made possitively conscious of the change-over setting of the treating mode irrespective of whether or not a previous treatment of the decomposing treatment mode for the larger amount of garbage is the same treatment mode or the ordinary treating mode, and so on.

According to the present invention, the foregoing objects can be realized by means of a garbage treating apparatus which comprises a treating vessel for accommodating a fermentative garbage decomposing agent carrying a microparasite and allowing the garbage thrown into the vessel for mixing with the agent for a decomposing treatment of the garbage, wherein means is provided for performing the decomposing treatment of the garbage in the treating vessel in a plurality of treating modes in a mutually exchangeable manner.

Further according to the present invention, the apparatus may be provided with means for changing over the mode of the decomposing treatment of the garbage, for example, from one treating mode to the other treating mode, and further with means for properly controlling the treating time of a selected one of the treating modes. In addition, it is also possible to employ means for improving mixing efficiency of the garbage with the fermentative garbage decomposing agent carrying the microparasite in the treating vessel.

According to the foregoing arrangement of the present invention, it is possible to include, for example, a strong treating mode in addition to the ordinary treating mode as a treating aspect of the decomposing treatment of the garbage thrown-in, whereby the garbage can be treated in an optimum mode in accordance with the amount of garbage thrown-in. It is also made possible to prevent such state causing the energy loss as the excessive dry from occurring, even in the absence of the user for several days without any control of the treating mode or any further throw-in of garbage.

Other objects and advantages of the present invention shall become clear as the description of the invention advances in the followings with reference to preferred embodiments shown in accompanying drawings.

Figure 1:
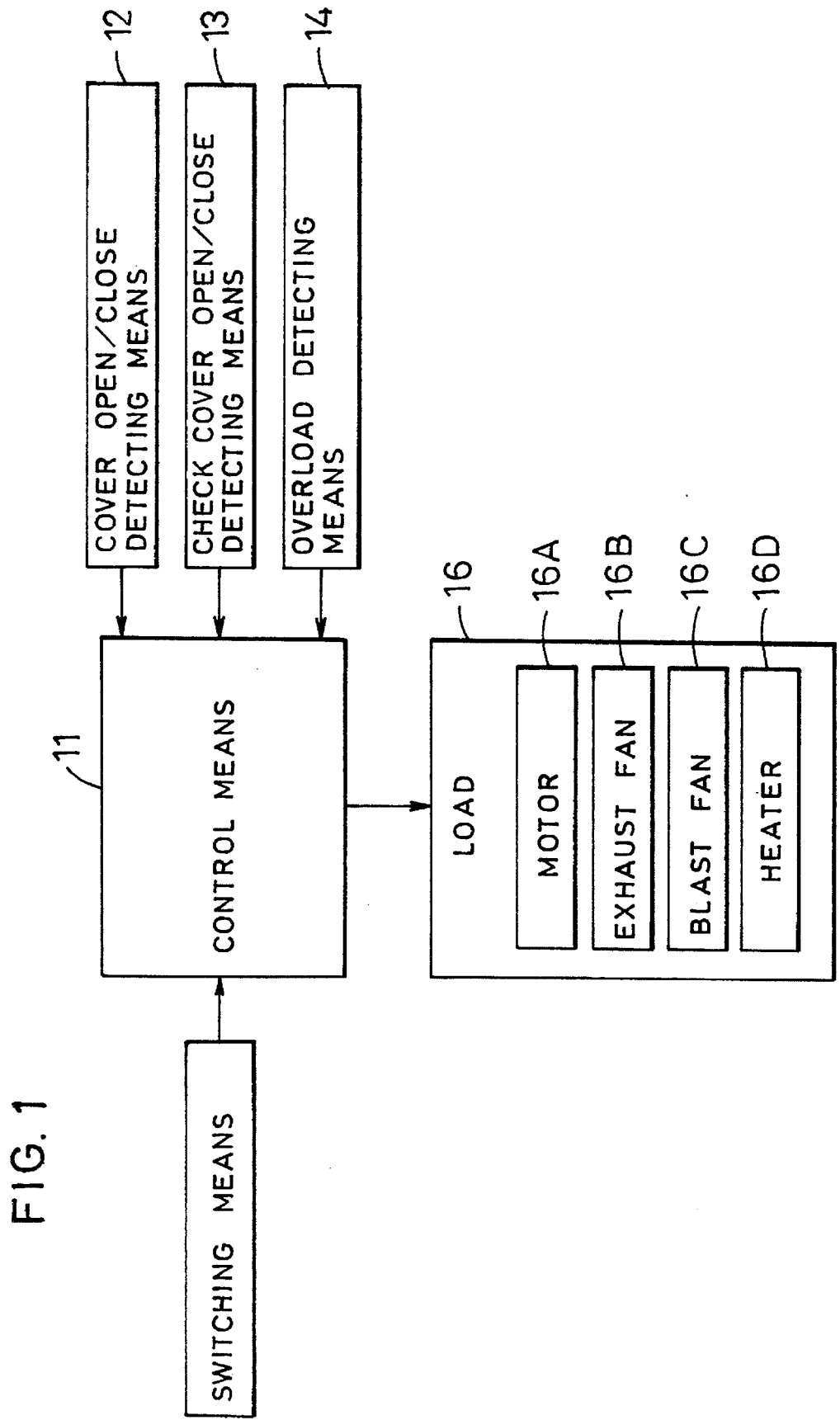
FIG. 1 shows in a schematic block diagram an embodiment of the garbage treating apparatus according to the present invention.

While the present invention shall now be described with reference to the embodiments shown in the drawings, it should be appreciated that the intention is not to limit the present invention only to these embodiments shown but to include all alterations, modifications and equivalent arrangements possible within the scope of appended claims.

DETAILED DESCRIPTION OF THE PREFERRED EMBODIMENTS

Referring to FIG. 1, there is shown in a block diagram the garbage treating apparatus according to the present invention, which apparatus includes a control means 11, and this control means 11 is provided for receiving respective outputs of a cover open/close detecting means 12, a check cover open/close detecting means 13, and an overload detecting means 14, while a switching means 15 is connected to the control means 11 for providing thereto ON/OFF signals. Further, the control means 11 is connected to a load circuit 16 for properly providing thereto controlling outputs, while the load circuit 16 includes, for example, a motor 16A, an exhaust fan 16B, a blast fan 16C and a heater 16D.

In the present instance, the cover open/close detecting means 13 detects opening and closing operation of the top cover upon throwing of the garbage into the apparatus. The control means 11 provides the controlling signals to the load circuit 16 so that a driving power for such loads as the motor 16A, exhaust fan 16B, blast fan 16C and heater 16D is made ON or OFF. More specifically, the detection by the cover open/close detecting means 12 of the opening of the cover causes one or more of the loads in the load circuit under the conditions set at the control means 11. Here, the switching means 15 employs preferably a limit switch, so that the opening and closing of the cover may be detected separately from the cover open/close detecting means 12 and the motor 16A may optimumly be made ON and OFF through the control means 11 independently of other loads.

Thus, as the cover is opened and the garbage is thrown in, the opening of the cover is detected by the cover open/close detecting means 12 and switching means 15, upon which the exhaust and blast fans 16B and 16C are turned ON while the motor 16A is turned OFF. At this time, as will be described in the following, the motor 16A for actuating the rotary shaft which mixes the garbage with the fermentative garbage decomposing agent within a treating vessel having the cover is stopped, so that the user's hands can be prevented from being hurt by the rotation of the rotary shaft and the safety can be maintained. On the other hand, the exhaust and blast fans 16B and 16C are rotated so that any leakage of offensive smell upon the opening of the cover can be restrained.

When the opening of the cover is detected by the detecting means 12, further, the arrangement is so made that the control means 11 turns OFF the motor 16A and turns ON the exhaust and blast fans 16B and 16C while the switching means 15 also acts to perform the same turning ON and OFF separately, then any danger caused by the rotary shaft rotated upon the throwing in of the garbage can be avoided in double manner with a backup of cover opening and closing by the switching means 15.

The check cover open/close detecting means 13 is provided for detecting the opening and closing of a check cover provided to the treating vessel as will be described in the followings, so that, upon detection of the opening of the check cover, the motor 16A is stopped through the control means 11 and any danger caused by the rotary shaft being rotated can be avoided. The overload detecting means 14 is provided for detecting any overload on the motor 16A so that, when the load incurred on the rotary shaft exceeds a predetermined value, the motor 16A is stopped to be able to avoid any occurrence of trouble in advance.

According to a remarkable one of features of the present invention, a plurality of modes of treating the garbage can be realized by the control means 11 as various garbage treating aspects, and the arrangement is so made that, as one of the various aspects, a strong treating mode is provided for realizing the decomposing treatment in a stronger manner than the normal treating mode. The arrangement can be modified to provide, in addition to the normal treating mode, four phases including strong, weak and weakest treating modes, or five phases including four aspects of the strongest, strong, weak and weakest treatments, which five phases in total are provided for mutual changeover operation.

Further, it is optimum that, in the garbage treating arrangement for realizing two phases treating mode of the normal and strong modes, the normal treating mode is automatically restored after passage of a predetermined period from execution of the strong treating mode. That is, in an event where the garbage is thrown into the apparatus every day substantially at a fixed time, for example, a setting of the mode for terminating the strong treating mode two to three hours before the fixed time will allow the user to reliably set the treating mode at a next time of throwing the garbage. In an event when the user stays away for several days, it is useful for the restraint of energy loss to change over the set mode of the strongest or strong treatment to another treating mode or, if necessary, to have the respective modes changed over stepwise over to the weakest treating mode. It should be also appreciated that the arrangement may be so made, when the treating mode is set to be other mode than the normal treating mode, as to have the normal treating mode restored always simultaneously with the cover opening, and that the changeover of the treating mode can be realized by the control means 11.

Figure 2:
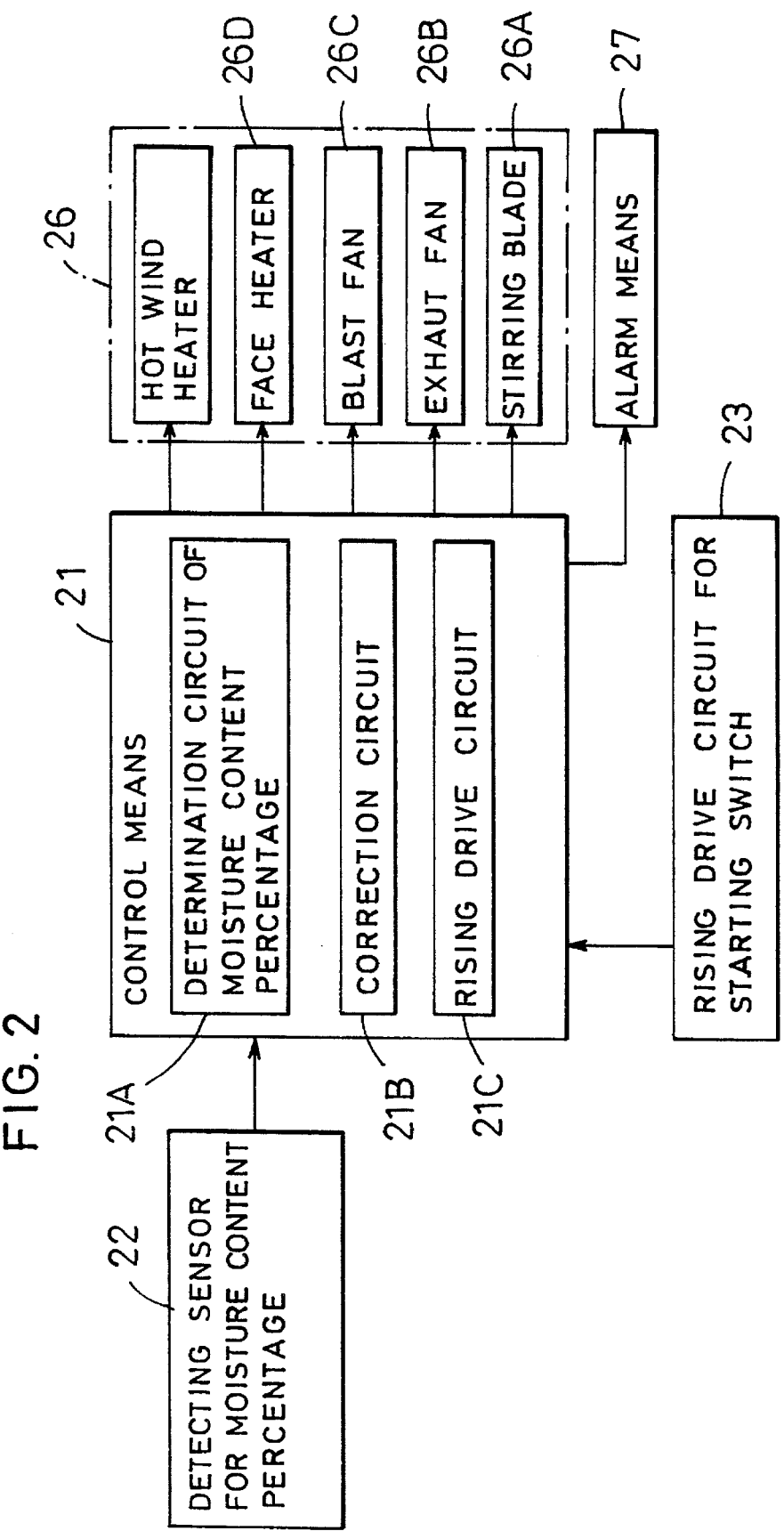
FIG. 2 is a schematic block diagram of another embodiment of the present invention.

In FIG. 2, there is shown another embodiment of the apparatus according to the present invention, in which the basic arrangement is similar to that of the embodiment of FIG. 1 but the control means 21 is connected to a moisture content sensor 22 for sensing the moisture content of the mixture of garbage and decomposing agent and a rising-drive circuit starting switch 23 for receiving signals from them, and to the load circuit 26 and an alarm means 27 for providing signals to them, while the control means 21 includes a moisture content determining circuit 21A, correction circuit 21B and rising-drive circuit 21C. In the load circuit 26, the heater 26D is divided into a hot-air blower and a surface heater.

In the present embodiment, the control means 21 is capable of turning ON and OFF one or more of such loads in the load circuit 26 as the rotary-shaft driving motor 26A, exhaust fan 26B, blast fan 26C, hot-air blower and surface heater of the heater 26D. For the treating aspects, such treating modes as shown in a following Table may be employed, in which the modes A through D denote the weakest, weak, normal and strongest treating modes respectively.

TABLE

| | Ext. Temp. | Treat. Mode Moist. Cont. | A less than 65% | B less than 65% | C more than 65% | D more than 65% |
|---|---|---|---|---|---|---|
| Load: Surface Heater: | | | | | | |
| Temp. Control | | | OFF | 9/11 | 9/11 | 39/41 |
| Output % | −5 | | OFF | 100 | 100 | 100 |
| | 5–15 | | OFF | 90 | 90 | 90 |
| | 15– | | OFF | 80 | 80 | 80 |
| Hot-Air Blower: | | | | | | |
| Temp. Control | −0 | | OFF | 6/8 | 12/14 | 39/41 |
| | 0–5 | | " | " | 14/16 | " |
| | 5–10 | | " | " | 16/18 | " |
| | 10–15 | | " | " | 18/20 | " |
| | 15– | | " | " | 19/21 | " |
| Output % | | | OFF | 50 | 75 | 100 |
| Exh. & Blast Fans | | | weak | weak | Norm. | Strgst. |
| Stir. Freq. | | | 1/24 H | 1/60 H | 1/60 H | 1/30 H |

In the Table, "19/21" means that the load is turned ON at 19° C. and turned OFF at 21° C., and "1/60H" means that the motor is rotated, after being stopped for 59 minutes, for 30 seconds in forward direction and, after being stopped for 3 seconds, for 27 seconds in reverse direction.

In executing the treating modes of the above Table, the control means 21 performs its controlling operation depending on whether the moisture content value determined by the moisture content sensor 22 in respect of the mixture of the garbage and decomposing agent is above or below such a predetermined value as 65%, such that, when the moisture content is above 65%, a moisture content regulating means (the load circuit in the embodiment shown) is shifted onto a side higher in moisture evaporating ability, that is, to a "normal evaporating mode" or "strongest evaporating mode" and, when the moisture content is below 65%, the moisture content regulating means is shifted onto a side lower in the moisture evaporating ability, that is, to a "weak evaporating mode" or "weakest moisture evaporating mode".

When, on the other hand, the moisture content value determined by the sensor 22 in respect of the mixture is below 65%, the control means 21 executes the control so as to have the apparatus operated in the "weak evaporating mode" on the low evaporating side. Further, when the opening of the cover for the treating vessel is not detected during the operation in the "weak evaporating mode", the arrangement may be so made that the mode is automatically changed over to the "weakest evaporating mode" after passage of a fixed period, for example, 72 hours. When the moisture content above 65% is reached, thereafter, the arrangement is so made as to shift the treating mode for the state of below 65% to the "normal treating mode" of the higher evaporating mode. When the moisture content below 65% is detected in the state of the higher evaporating mode, contrarily, the arrangement is so made as to automatically shift the mode to the lower evaporating mode side.

Further, in order to prevent any erroneous determination by the sensor 22 of the moisture content, an average value of a plurality of measurement of a temperature rising degree $\Delta T$ ($=T_1-T_0$) obtainable on the basis of an initial temperature $T_0$ at the time when the heater 26D is energized and an elevated temperature $T_1$ after passage of a predetermined period from the energization of the heater 26D is taken, and the correction circuit 21B operates to obtain accurate moisture content while remarkably reducing the error in view of the average value. Further, when the operation on the side of the lower evaporating mode or of the higher evaporating mode continues for more than a predetermined, this fact is alarmed by the alarm means 27 connected to the control means 21, so that an excessively moistened or dried state of the mixture being treated can be prevented from occurring. For this alarm means 27, a light emitting diode or the like may be employed for executing the alarm by repeating ON/OFF states of the diode.

The correction circuit 21B of the control means 21 is provided for correcting any fluctuation in output values of the moisture content sensor 22 by measuring output characteristics of the moisture content sensor 22 and changing over the data for obtaining the moisture content from the temperature rising degree $\Delta T$ by means of a changeover switch. While there is a risk that the microparasite carried by the fermentative garbage decomposing agent cannot be sufficiently activated in the initial period of the operation of the apparatus, the control means 21 in the present instance is provided with a rising-drive circuit 21C, so that the starting switch 23 connected to the control means 21 causes the circuit 21C to start so as to have the operation on the high evaporating side, in particular, the highest evaporating mode executed positively in the initial period of the operation, and the rotary shaft and heater are operated for a positive activation of the microparasite of the fermentative garbage decomposing agent.

Figure 3:
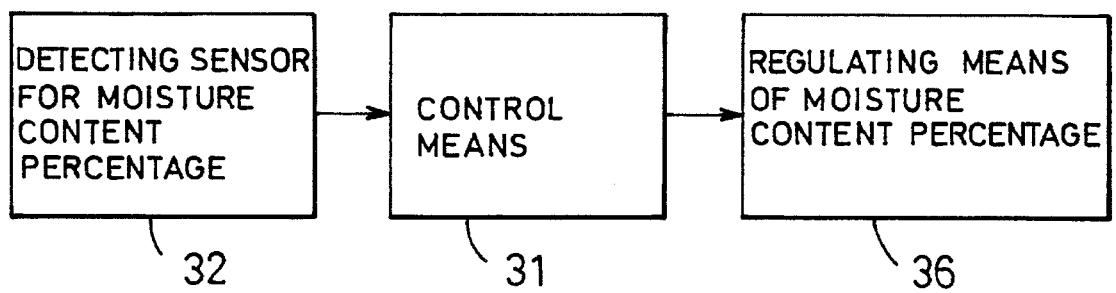
FIG. 3 is also a schematic block diagram showing still another embodiment of the present invention.
Figure 4:
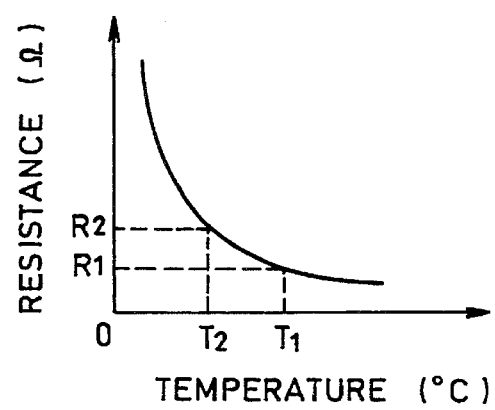
FIG. 4 is a graph showing the relationship between the temperature and the resistance of negative characteristic thermistor employed in the garbage treating apparatus according to the present invention.
Figure 5:
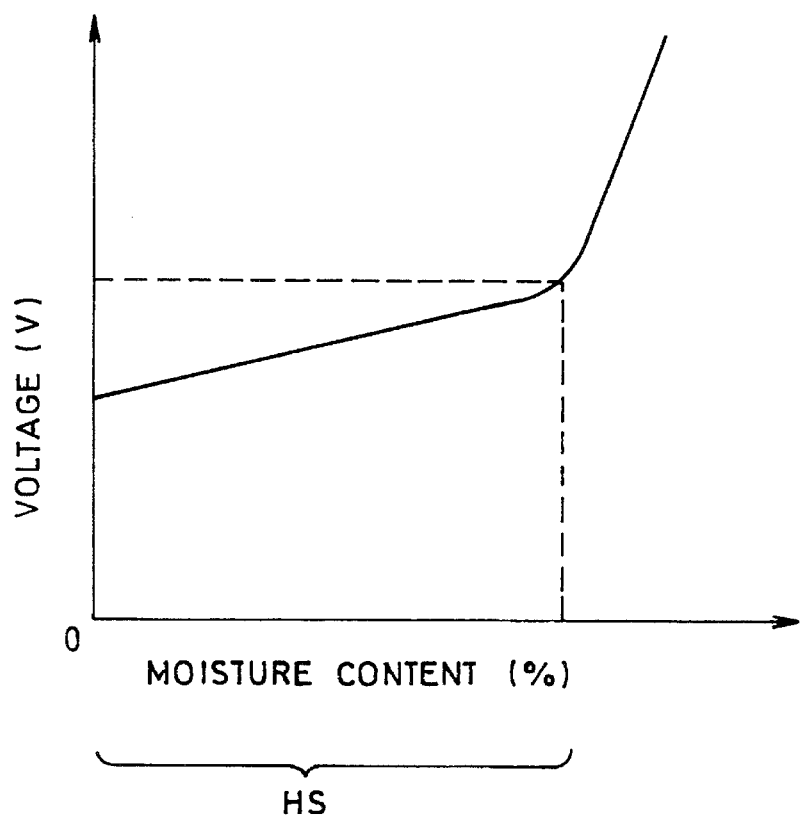
FIG. 5 is a graph showing the relationship between the voltage of the negative characteristic thermistor in FIG. 4 and the moisture or water content of a mixture of the garbage and fermentative decomposing agent.
Figure 6:
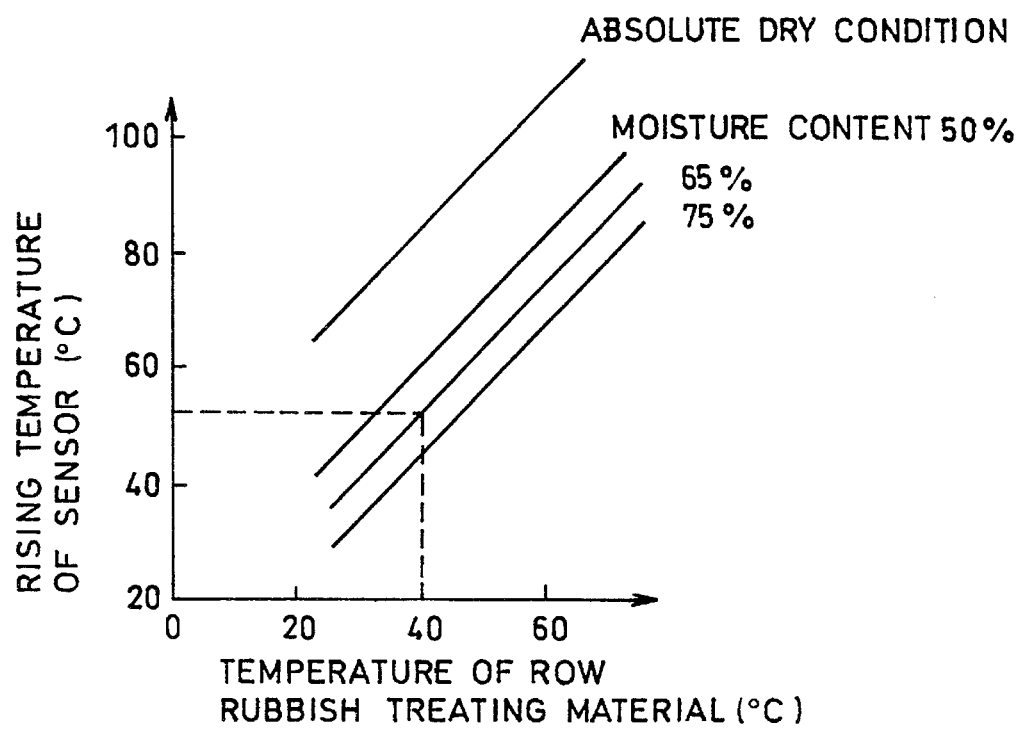
FIG. 6 is a graph showing the relationship between the rise in the temperature of the negative characteristic thermister of FIG. 4 and the temperature of the mixture of the garbage and decomposing agent.
Figure 7:
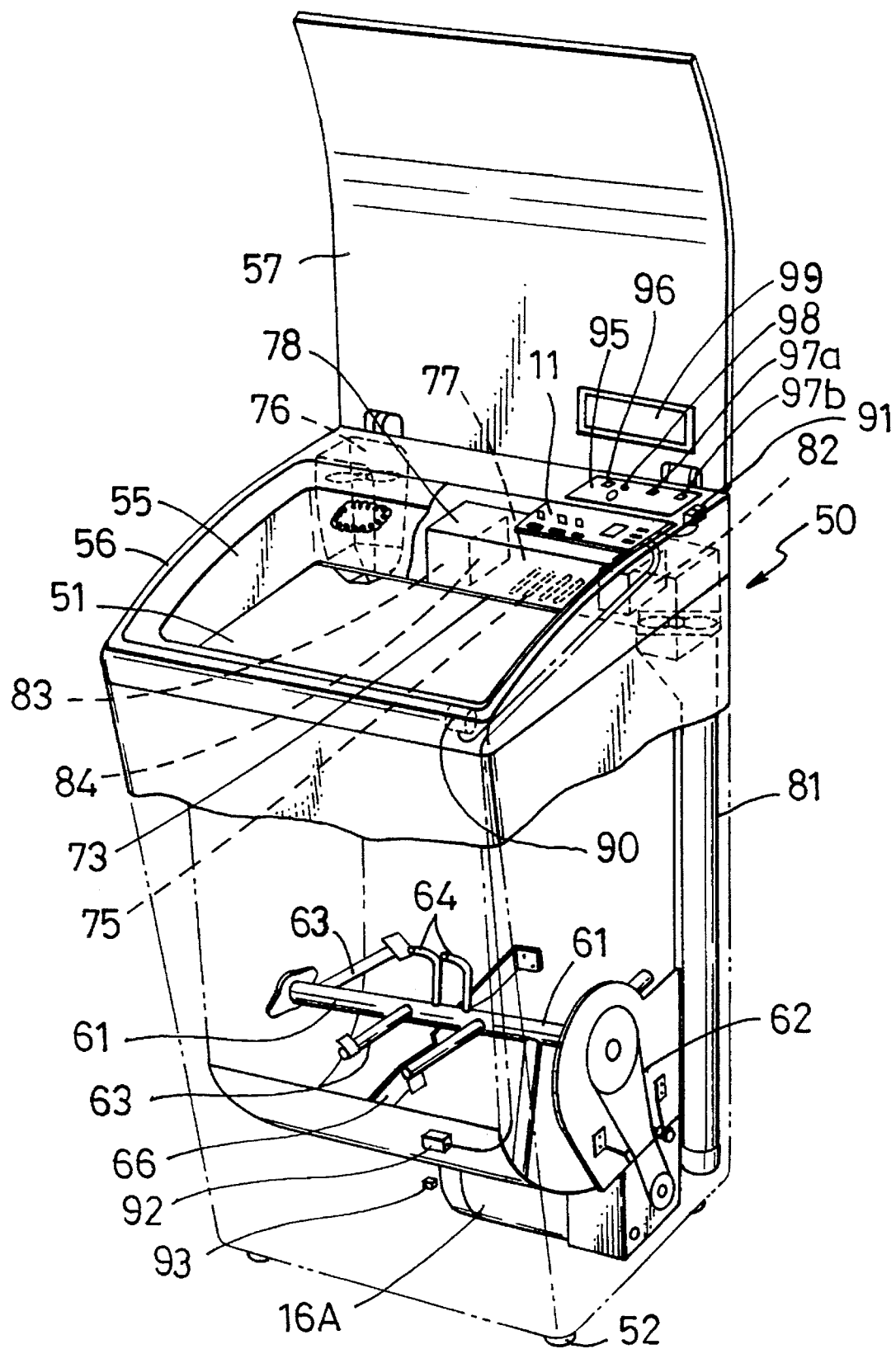
FIG. 7 shows in a perspective view the entirety of the apparatus for realizing the embodiments of the present invention with part of a side cover of the apparatus removed.
Figure 8:
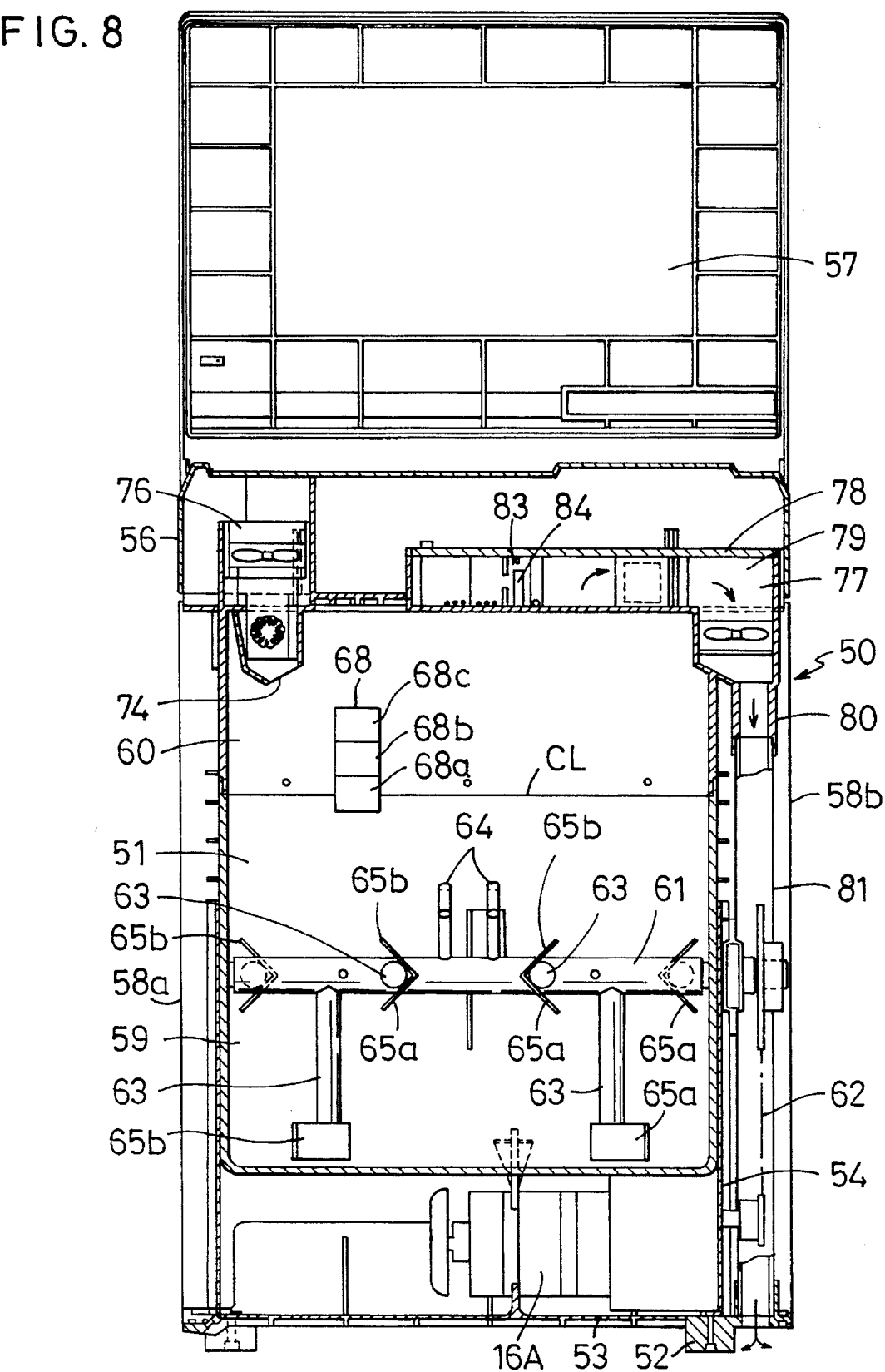
FIG. 8 is a vertically sectioned view of the apparatus shown in FIG. 7.
Figure 9:
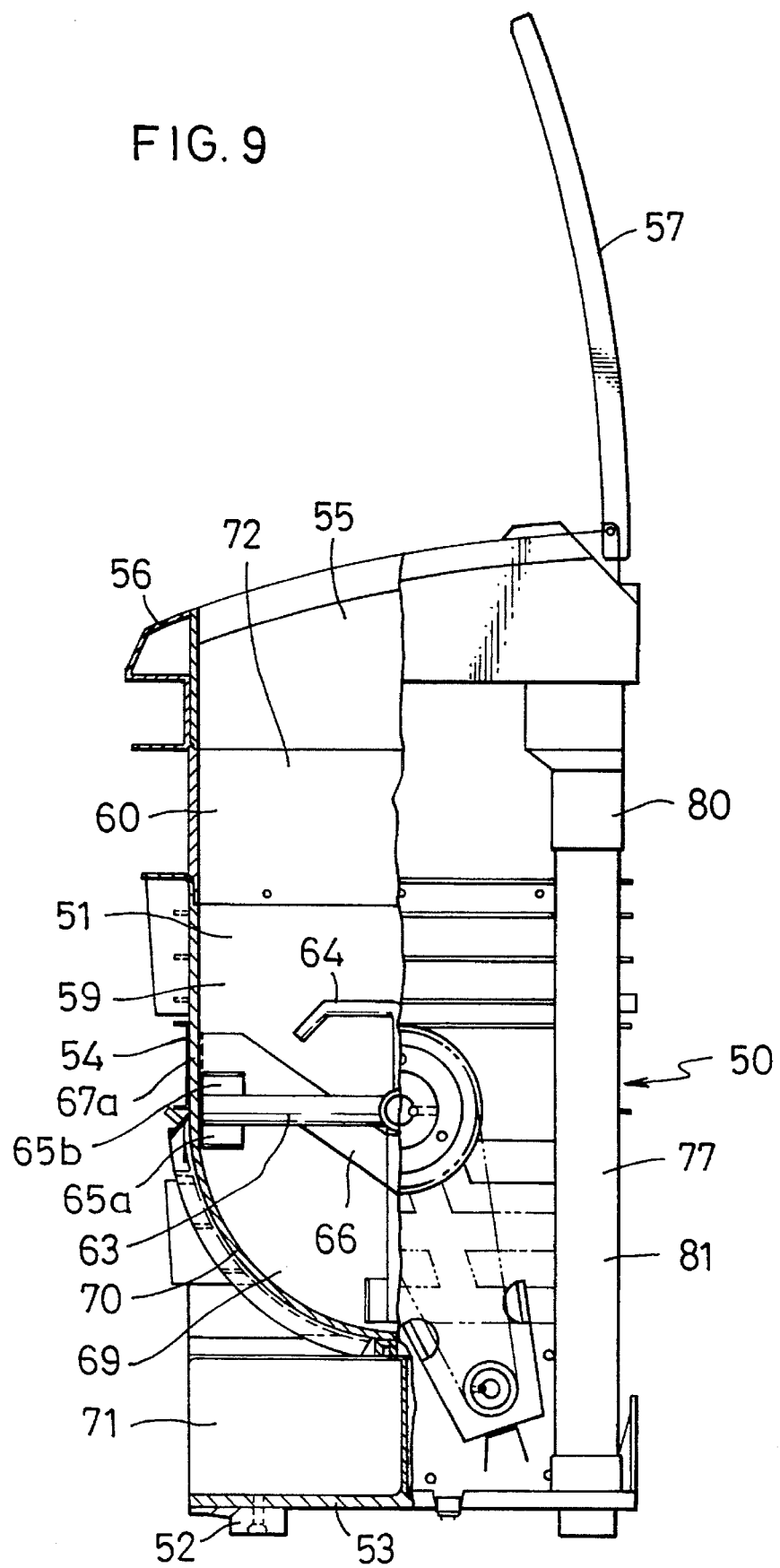
FIG. 9 is a side elevation of the apparatus of FIG. 7 with certain parts shown as removed.
Figure 10:
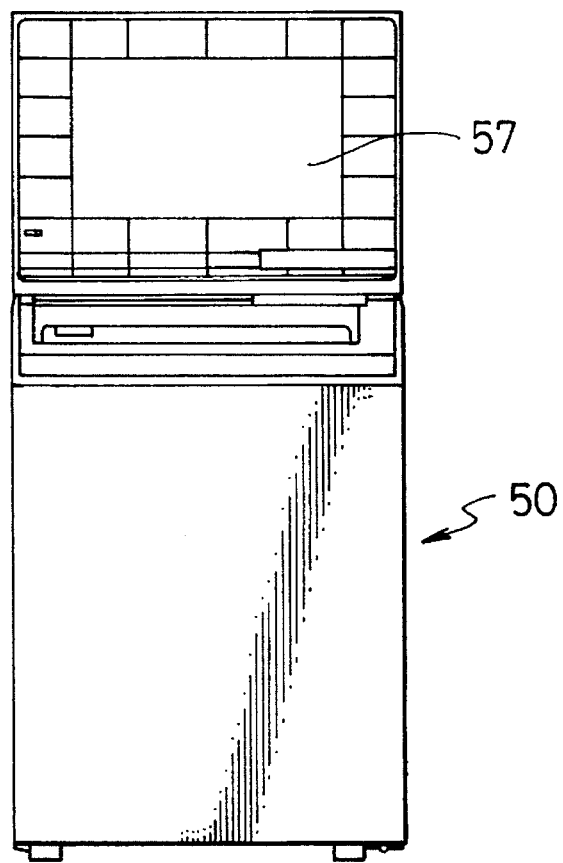
FIG. 10 is a front side view of the apparatus of FIG. 7 with a top cover shown as opened.
Figure 11:
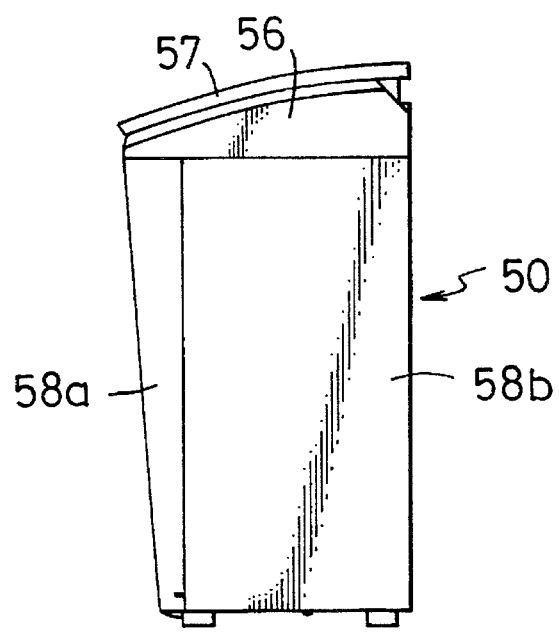
FIG. 11 is also the side elevation of the apparatus of FIG. 7 with the top cover shown in closed state.
Figure 12:
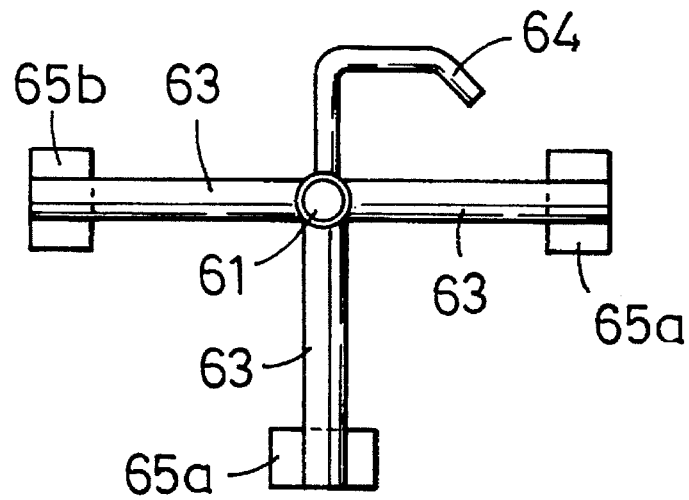
FIG. 12 is a side elevation of the rotary shaft employed in the apparatus of FIG. 7.
Figure 13:
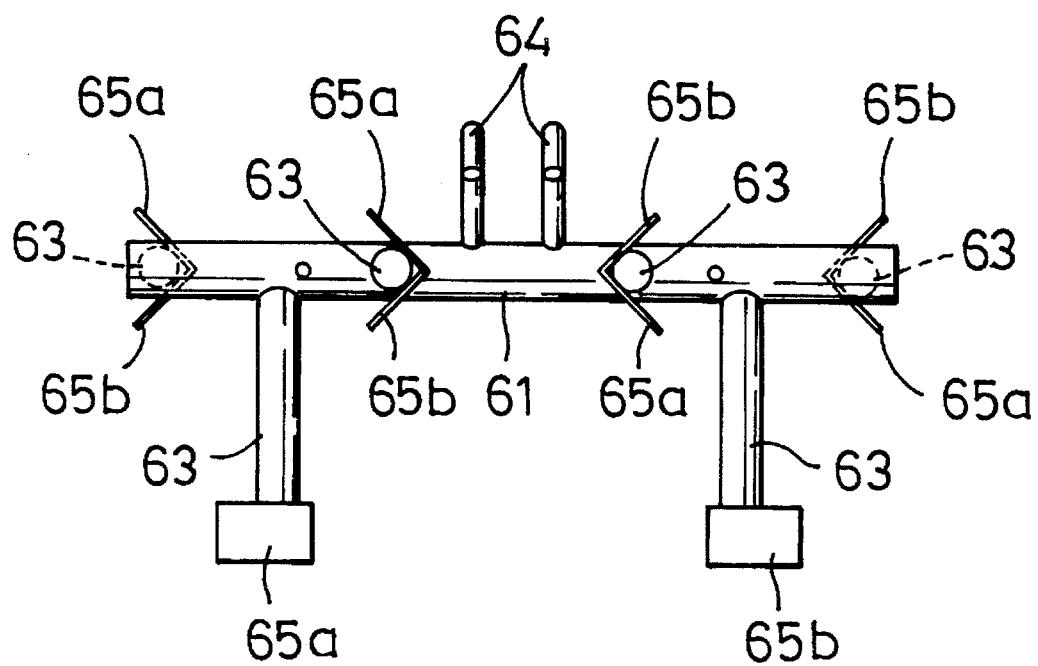
FIG. 13 is a front side view of the above rotary shaft.
Figure 14A:
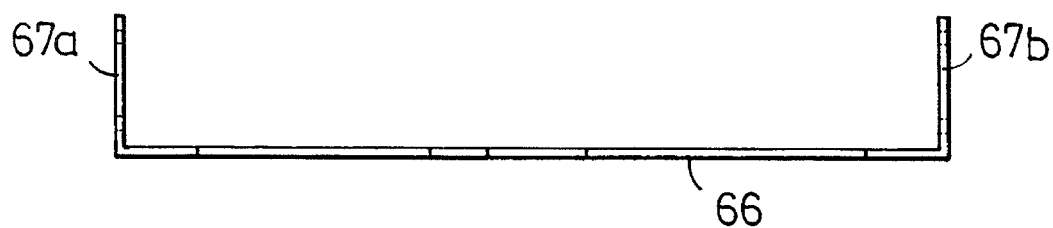
FIG. 14A is a fragmentary plan view of the rorary shaft.
Figure 14B:
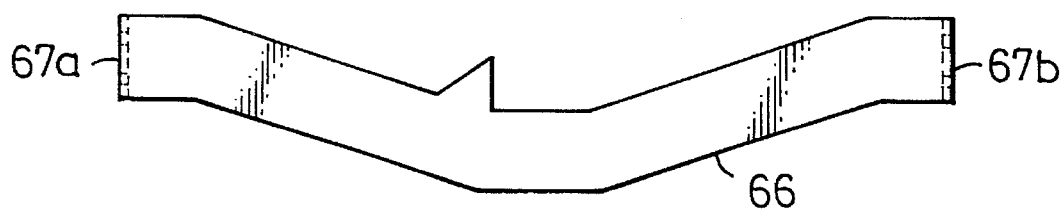
FIG. 14B is a fragmentary plan view also of the rotary shaft.
Figure 14C:
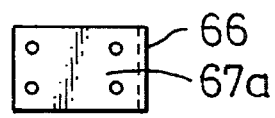
FIGS. 14C and 14D are partial side elevations of the rotary shaft.
Figure 14D:
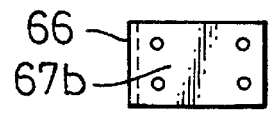

In FIG. 3, there is shown still another embodiment according to the present invention, which is similar in the basic arrangement to the embodiment of FIG. 1, but in the present instance the moisture content sensor 32 and moisture-content regulating means 36 are connected to the control means 31, and a negative characteristic thermistor is employed in the moisture content sensor 32. This negative characteristic thermistor has such resistance-to-temperature relationship as shown in FIG. 4 and, when the same is not brought into contact with a coolant, shows a low resistance R1 with the temperature kept at a higher temperature T1 (°C.) but, once brought into the contact with the coolant, a high resistance R2 as raised from R1 with the temperature lowered from T1 (°C.) to T2 (°C.), whereby the voltage is caused to rise. Consequently, the garbage mixed in the treating vessel with the garbage treating agent is caused to be decomposed by the microparasite thus activated and to generate water, which water is absorbed by the garbage decomposing agent to elevate the moisture content of the mixture, while the negative characteristic thermistor disposed within the treating vessel and brought into contact with the decomposing agent which contains thus absorbed water becomes large in heat radiation amount to be decreased in the temperature, and the resistance of the thermistor rises to also raise the voltage, as seen in FIG. 5 showing the relationship between the voltage of the negative characteristic thermistor and the moisture content of the mixture. With the negative characteristic thermistor covered with an unwoven cloth or the like, the thermistor voltage shows to be sensitive to the moisture content of the mixture in a range shown by HS in the curve of FIG. 5. Now, as shown in FIG. 6, the moisture content of the mixture made high causes the heat radiation of the negative characteristic thermistor to be large, so that the moisture content increased renders the temperature rising degree to be smaller.

Referring now to FIGS. 7 to 11, a more practical arrangement of the garbage treating apparatus according to the present invention is shown, in which an apparatus housing 50 defines therein a treating vessel 51, while the housing 50 is mounted on a metal frame 54 fixed onto a bottom plate 53 having supports 52. At the top part of the housing 50, a cover frame 56 defining an opening 55 is mounted, and a top cover 57 is hinged to an edge of the cover frame 56 for the cover opening and closing rotation. Between the cover frame 56 and the bottom plate 53, front and side covers 58a and 58b are fitted.

The treating vessel 51 comprises preferably a lower vessel body 59 and an upper hollow part 60 continuous to the body 59, and a rotary shaft 61 is extended substantially horizontally within the vessel 51 as rotatably born at both axial ends by opposing side walls of the vessel body 59, while one axial end extends out of the vessel body 59 to be linked to an output shaft of the motor 16A fixed to the frame 54 through such drive-power transmitting means 62 as a chain, for being axially rotated. A plurality of stirring arms 63 are secured to the rotary shaft 61 to extend radially therefrom at different positions along the length of the shaft, and a pair of coarse crushing blades 64 are also secured to central part of the rotary shaft 61. While the stirring arms 63 are formed optimumly in a bar shape, they need not be so limited, and are provided at extended tip ends with guiding flaps 65a and 65b secured for shifting a mixture of the garbage with the decomposing agent towards the centrally positioned coarse crushing blades 64.

Figure 15:
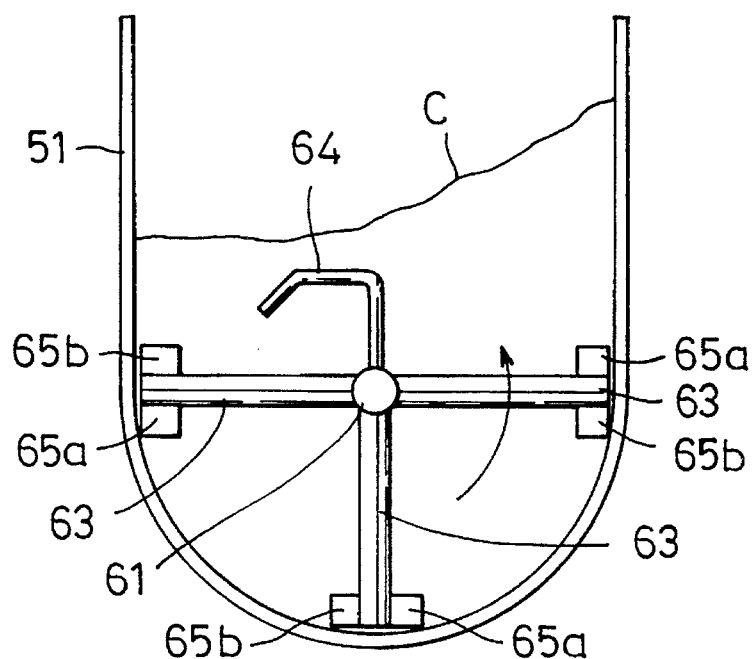
FIG. 15 is an explanatory view for the operation of the rotary shaft in the apparatus of FIG. 7.

The motor 16A is of a reversible type, preferably, so that the rotary shaft 61 may be rotated in both of forward and reverse directions, and the guiding flaps 65a and 65b are formed to include ones 65a contributive to the shifting of the mixture towards the central coarse crushing blades 64 in the forward directional rotation of the shaft 61 and ones 65b contributive to the same shifting of the mixture in the reverse directional rotation of the shaft 61. Further, the coarse crushing blades 64 are formed as bent at least in one rotating direction for increasing catching power with respect to the garbage upon being rotated, and a stationary blade 66 as shown in FIGS. 14 and 15 is disposed to extend a space between the pair of the coarse crushing blades 64 to intersect substantially at right angles the rotary shaft 61, as secured at both fixing end parts 67a and 67b to other opposing walls of the vessel body 59. Since the coarse crushing of some stuff contained in the garbage requires a relatively large force, extended length of the coarse crushing blades 64 should preferably be limited to be relatively shorter than that of the stirring arms 63, so that the blades can be rotated by a relatively smaller drive force.

While the treating vessel 51 is provided for throwing therein the garbage through the opening 55, the known fermentative decomposing agent consisting of wooden chips and carrying at least a microparasite effective to the decomposing treatment of the garbage is also put into the vessel to be mixed with the garbage. In this case, the garbage and its decomposing agent are put into the vessel 51 up to a charge level CL shown in FIG. 8, and a visually level confirming member 68 is provided to an inner wall of the vessel 51, which member 68 including a normal level indication 68a, a warning level indicator 68b and an abnormal level indicator 68c, while these indicators should preferably be colored in blue, yellow and red, respectively for easy visual confirmation of the level. Thus, the visual level confirming member 68 comprises the normal, warning and abnormal level indicators sequentially stacked from below so that, when the level of the mixture of the garbage and decomposing agent exceeds the blue, normal level indicator 68*a* and reaches the yellow warning level indicator 68*b* or the red abnormal level indicator 68*c*, the throw-in of the garbage is ceased and the treating mode is changed over, if required, to the strong streating mode, so as to have the mixture level lowered to the normal level indicator 68*a*.

Figure 16:
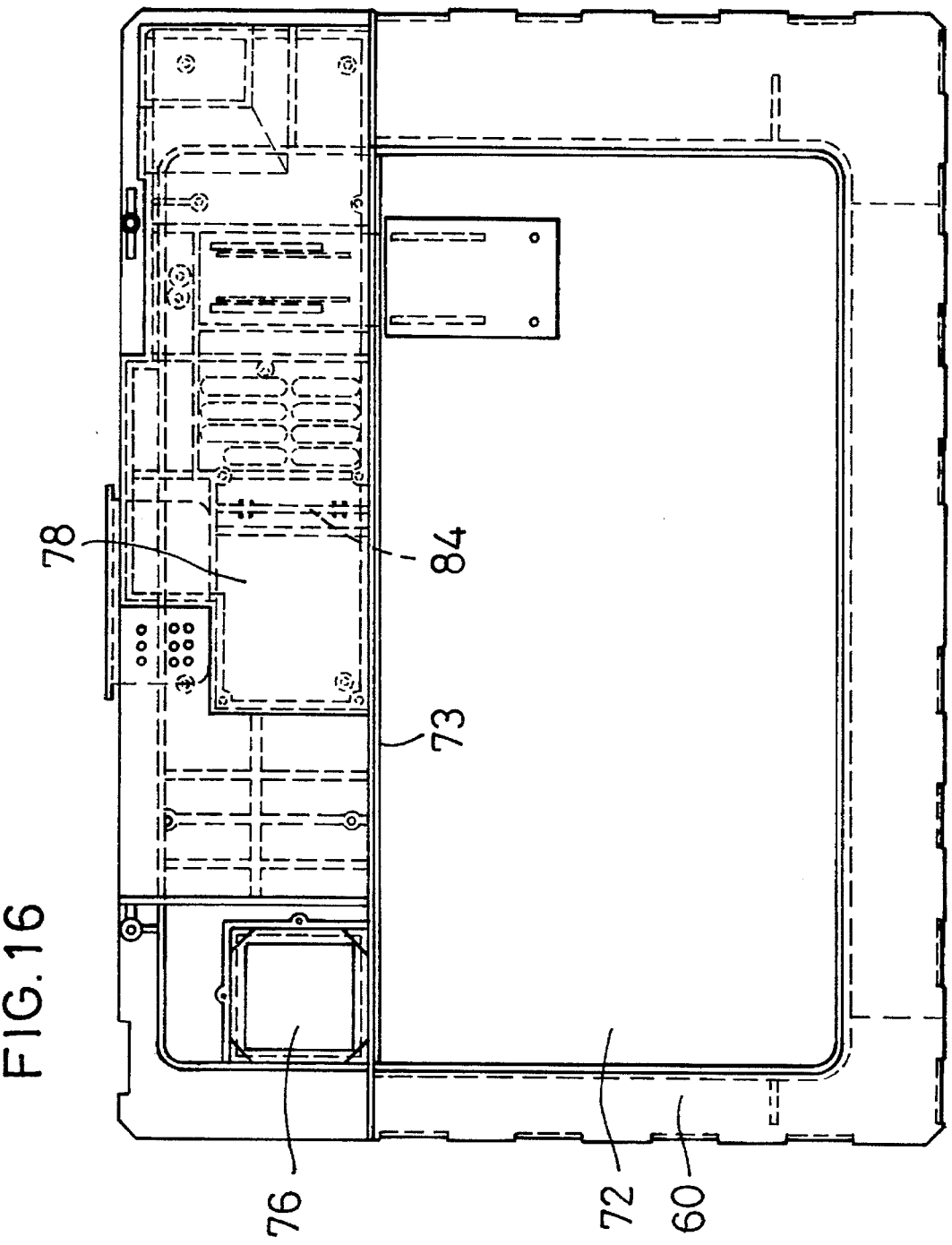
FIG. 16 is a plan view at top housing of the apparatus shown in FIG. 7.
Figure 17:
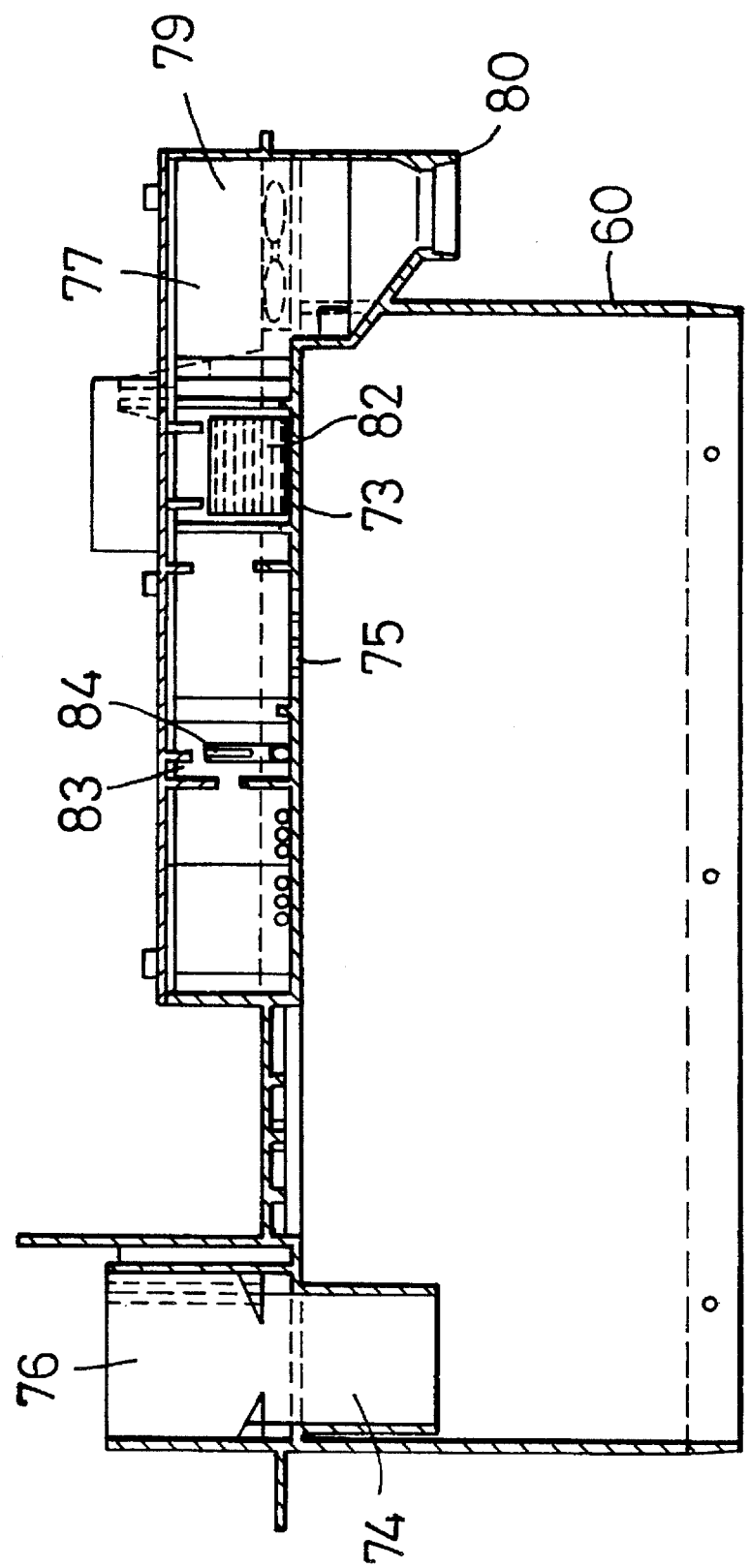
FIG. 17 is a sectioned view at the top housing of FIG. 16.

In the bottom part of the treating vessel 51, there is provided a check port 69 which is covered by a check cover 70 mounted to the vessel for opening and closing the check port 69. The bottom plate 53 is provided with a receiving recess 71 while, as shown in FIGS. 16 and 17, the upper hollow part 60 of the treating vessel 51 is provided with a throw-in port 72, and a flange 73 is provided at an edge of the throw-in port 72 to extend inward the treating vessel 51. This flange 73 is formed to have a blast port 74 and an exhaust port 75 in bottom plate part. The blast port 74 is positioned at an end of a blast path 76 the other end of which is opened to the atmosphere, while the foregoing blast fan 16C, heater 16D and so on are disposed in the blast path 76. The exhaust port 75 is positioned at an end of an exhaust path 77, and this exhaust path 77 comprises an exhaust fluidizing part 79 formed as defined between the flange 73 and an upper plate 78 mounted above the flange 73, and an exhaust duct 81 provided at an end of the exhaust fluidizing part 79 to be continuous to a connecting cylinder part 80 disposed at outer top portion of the treating vessel 51 and extending downward along an outer side wall of the vessel 51. A lower end of the exhaust duct 81 is opened to lower side of the bottom plate 53 as shown in particular in FIG. 8. Here, the exhaust duct 81 is disposed to extend vertically along outer side surface of the treating vessel 51, utilizing a dead space adjacent to the drive-power transmitting means 62 on the outer side surface on one side of the treating vessel 51, so that the entire structure of the apparatus will be compact. In the exhaust path 77, further, there are provided a deodorant 82 and the exhaust fan 16B described with reference to FIGS. 1 and 2, in the order described in the direction from the exhaust port 75 to the connecting cylinder part 80, and the control means 11 described also with reference to FIGS. 1 and 2 is disposed on the upper plate 78.

At a position also between the flange 73 and the upper plate 78 but on the other side of the exhaust port 75, there is provided a space 83 for disposing an ozonizer and communicating with the exhaust path 77 through a communicating part disposed on an upstream side of the position of the deodorant 82 in the exhaust path 77. An ozonizer 84 is disposed in its disposing space 83 which is provided with an opening for leading the atmosphere into the space. Since deodorizing ability of the deodorant 82 is deteriorated after many hours by any offensive smell components absorbed by the deodorant 82, the ozonizer is actuated to generate ozon so as to cause ozon to react on the offensive smell components absorbed, and the deodorant 82 is thus regenerated.

The operation of the garbage treating apparatus according to the present invention shall now be described. The operation can be set by the control means 11 to be, for example, in such four modes as has been partly described, including the normal treating mode, strong treating mode, weak treating mode and weakest treating mode. The respective modes can be realized by properly regulating driving intervals of the motor 16A for the rotary shaft 61 having the stirring arms 63, detection temperature of the thermistor for turning the heater 16D ON, blasting rate of the blast fan 16C, and exhausting rate of the exhaust fan 16B. Now, in the normal treating mode, the treating is set to be able to treat about 700 to 1,000 g. of the garbage which is a normal throw-in amount of each ordinary family, and, the strong treating mode is set for treating about 1,000 to 1,500 g. of the garbage to be able to cope with a slightly larger throw-in amount of garbage. When the throw-in amount exceeds 1,500 g. to a remarkable extent, the garbage should be thrown in as divided into two groups.

In the event when the top cover 57 is opened and the garbage is thrown through the throw-in opening 55 into the treating vessel 51 in which the fermentative garbage decomposing agent is preliminarily placed, the motor 16A is turned OFF in response to the opening of the top cover 57 and the exhaust fan 16B is turned ON to start exhausting air inside the vessel through the exhaust path and duct 77 and 81 to the exterior, so that the rotary shaft 61 is kept in non-rotated state to allow the user to throw in the garbage in safe manner while being prevented from suffering offensive smell leaking out of the throw-in opening 55 by the air exhaustion. As the top cover 57 is closed and the motor 16A is turned ON, the rotary shaft 61 is rotated to stir and mix the garbage with the decomposing agent carrying the microparasite while bringing them into contact with air, and the garbage starts being decomposed by the microparasite carried by the decomposing agent. As the blast fan 16C is driven at this time, the atmosphere is led through the blast port 74 into the treating vessel 51 to be brought into contact with surface layer of the decomposing mixed with the treating agent so as to evaporate the moisture content from the decomposing agent, and the exhaust fan 16B being actuated causes the inside air made high in the moisture content to be discharged through the exhaust port 75 to the exhaust path 77, so that the exhaustion is performed from the path 77, through the exhaust duct 81 and the lower open end of the duct at the lower face of the bottom plate 53 to the exterior. Since exhaustion through the exhaust path 77 involves the deodorant 82 while being fluidized for absorption of the offensive odor components, the air discharged to the exterior of the apparatus does not accompany offensive smell.

While the rotation of the rotary shaft 61 causes the garbage to be excellently mixed with the decomposing agent by means of the stirring arms 63 and the mixture is crushed by the coarse crushing blades 64, the guiding flaps 65*a* and 65*b* of the stirring arms 63 are effective to shift the mixture of the garbage and decomposing agent towards the central part of the rotary shaft 61 where the coarse crushing blades 64 are provided, whereby the crushing action is improved and the decomposing function of the microparasite of the decomposing agent is also improved. As will be clear when FIG. 15 is referred to in particular, on the other hand, the rotation of the rotary shaft 61 in a single direction causes surface level C of the mixture to lean to be one-sided, and it is preferable to employ a reversible motor as the motor 16A so that the rotary shaft 61 can be driven as reversed after fixed intervals.

According to the present invention, further, the garbage treating apparatus is constituted for attaining various functions. Thus, a cover opening/closing detector 90 is provided to the housing 50, so as to constitute at least part of the cover open/close detecting means 12 shown in FIGS. 1 and 2. In this case, preferably, the cover frame 56 is provided with a lead switch for detecting the opening and closing of the top cover 57, and the respective loads 16 are properly made ON or OFF by a detection signals of the lead switch for realizing the foregoing operating modes. The check-cover open/close detecting means 13 is separately mounted to the housing 50 with respect to the check cover 70 for being actuated independently of the foregoing cover open/close detecting means 12, so that a detection signal of this means 13 can be provided to the control means 11, that is, an output of a check-cover open/close detector 92 forming at least part of the check-cover open/close detecting means 13 is utilized.

Further, the housing 50 is provided with such switching means 93 at a limit switch which is formed to be utilized for controlling the load 16 separately from the foregoing cover open/close detecting means 12 and check-cover open/close detecting means 13. The housing 50 is also provided with an overload detecting means 94 in respect of the motor 16A so that, when an overload is applied to the motor 16A, the control means 11 can stop the motor 16A. An operating state display 95 is further provided to the cover frame 56, and the display 95 includes mode display lamps for a mode changeover switch display 96, normal treating mode display 97a, strong treating mode display 97b and power source display 98. In addition, the top cover 57 has a transparent window 99 allowing the user to visually recognize the display 95 over the top cover.

Figure 18:
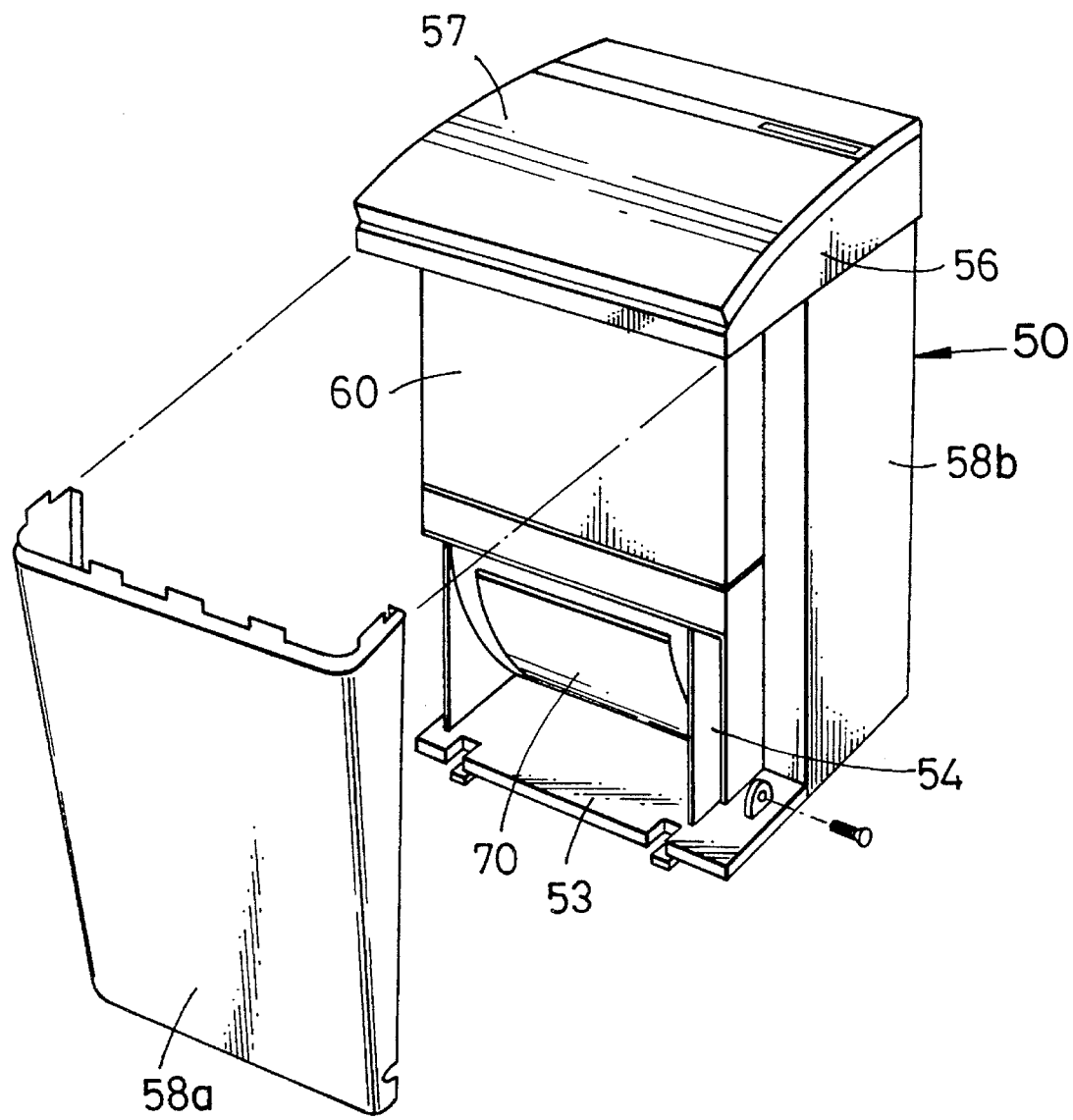
FIG. 18 is a perspective view with part disassembled of the top housing of FIG. 16.

As shown in FIG. 18, it is useful to mount the front cover 58a in a manner detachable with respect to the housing 50, for cleaning the interior of the treating vessel 51.

Figure 19:
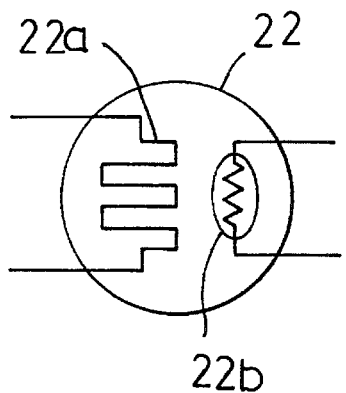
FIG. 19 is a schematic circuit diagram showing a practical example of a moisture content sensor employed in a garbage treating vessel of the garbage treating apparatus according to the present invention.
Figure 20:
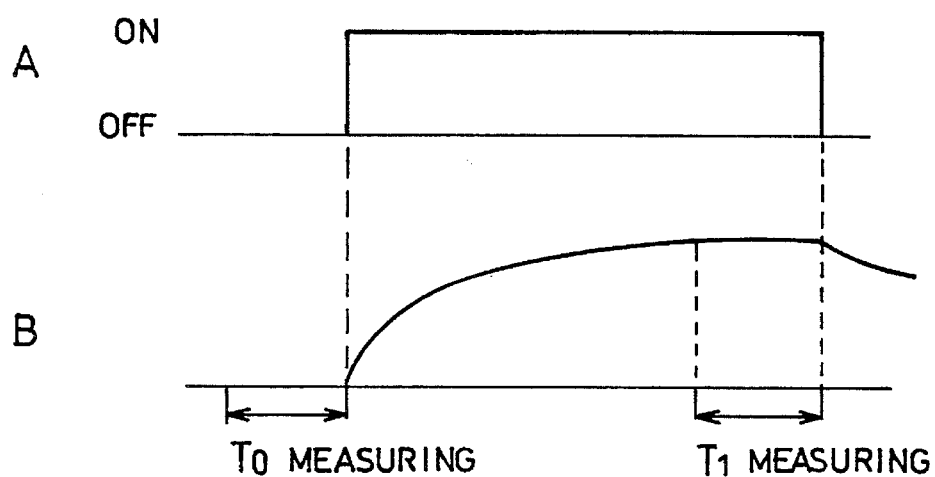
FIGS. 20A and 20B are time charts of the sensor shown in FIG. 19.
Figure 21:
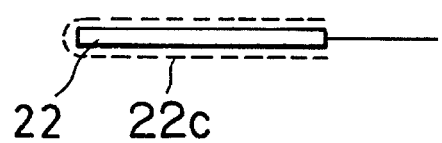
FIG. 21 is an explanatory view for an aspect of the negative characteristic thermistor employed in the sensor of FIG. 19.
Figure 22:
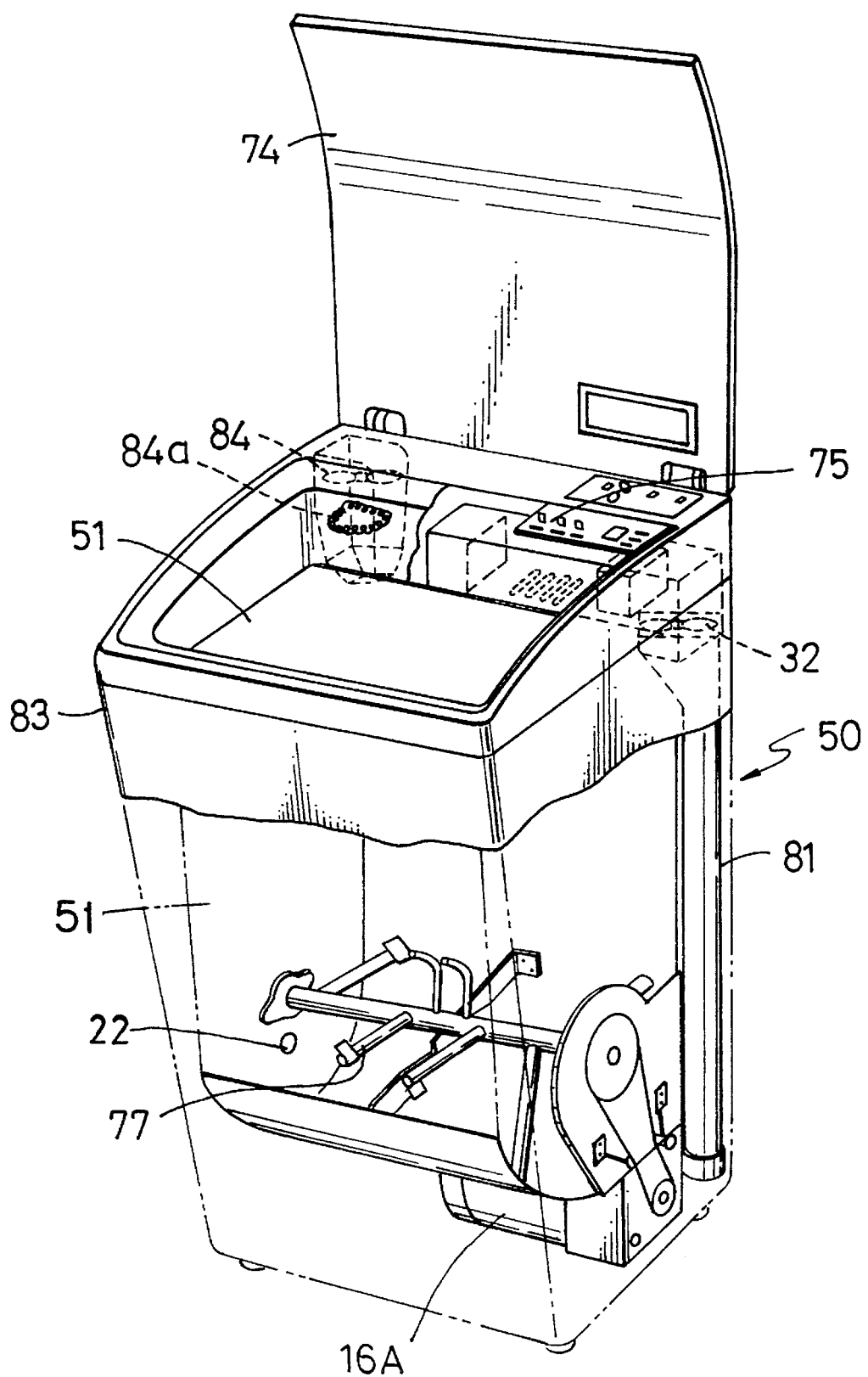
FIG. 22 shows in a perspective view, with part of body housing removed another working aspect of the embodiment according to the present invention.
Figure 23:
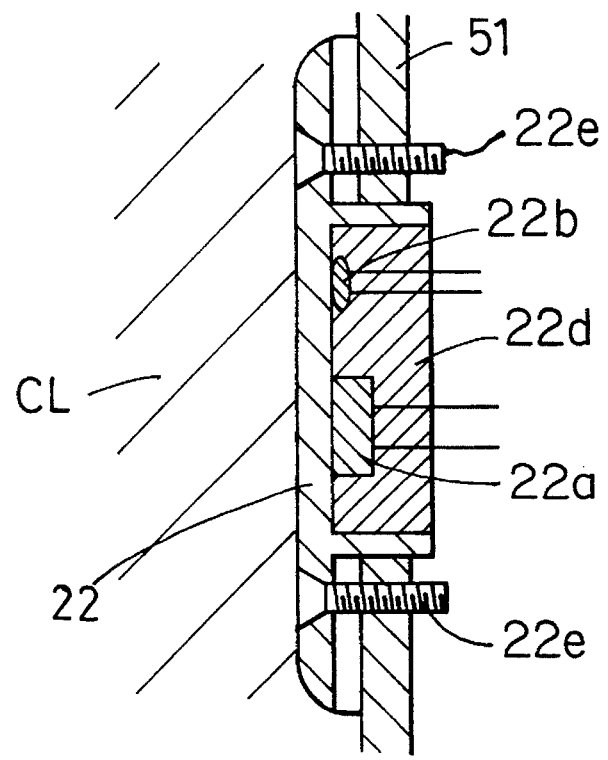
FIG. 23 shows in a fragmentary sectioned view a mounting state of the moisture content sensor employed in the garbage treating apparatus according to the present invention.

Further, in the moisture content sensor 22 employed in the present invention is formed by a thermistor 22a and heater 22b as shown in FIG. 19, and the moisture content detection is executed at predetermined intervals in respect of the mixture of the garbage with the treating agent, as will be clear when FIG. 20 is also referred to, in which a waveform A denotes the heater's heat and the other waveform B denotes the thermistor's temperature. It may be possible to improve the sensitivity of the thermistor by covering the same with an unwoven cloth 22c for causing moisture to be absorbed by this unwoven cloth, as shown in FIG. 21. Further, as shown in FIGS. 22 and 23, the sensor 22 may be secured integrally to the inner side wall of the treating vessel 51, in which event a casing of the sensor 22 is formed by such high heat conductive material as stainless steel, copper, aluminium and the like, a heat generating resistor 22b and thermosensor 22c are secured through a mold 22d to rear surface of the casing, of the sensor 22 and the casing is mounted to the inner wall of the treating vessel 51 by means of screws 22d, whereby the moisture content detection can be properly realized with respect to the mixture CL of the garbage and treating agent within the vessel 51.

Figure 24A:
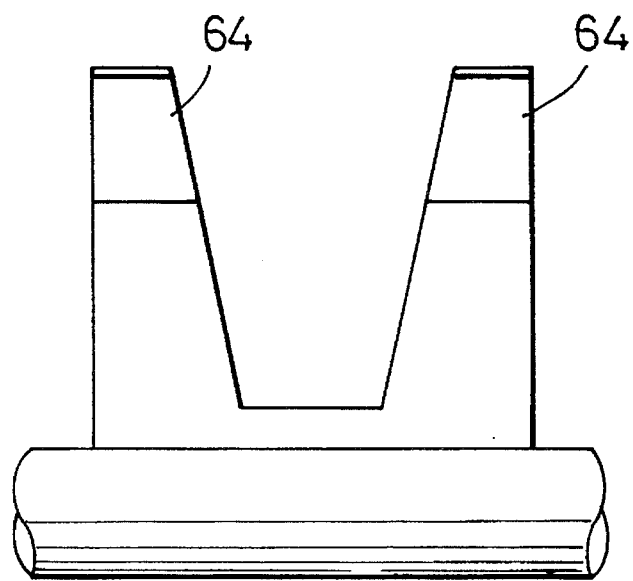
FIG. 24A is a fragmentary front view in another working aspect of the rotary shaft employed in the apparatus according to the present invention.
Figure 24B:
FIG. 24B is a fragmentary plan view of the rotary shaft of FIG. 24A.
Figure 25A:
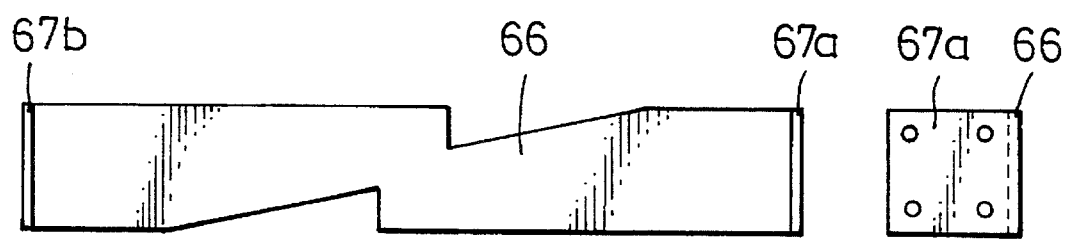
FIG. 25A is a fragmentary front view in another aspect of the rotary shaft.
Figure 25C:
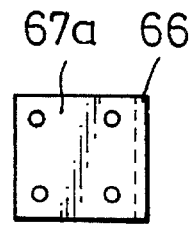
FIG. 25C is a side view of the rotary shaft of FIG. 25A.
Figure 25B:
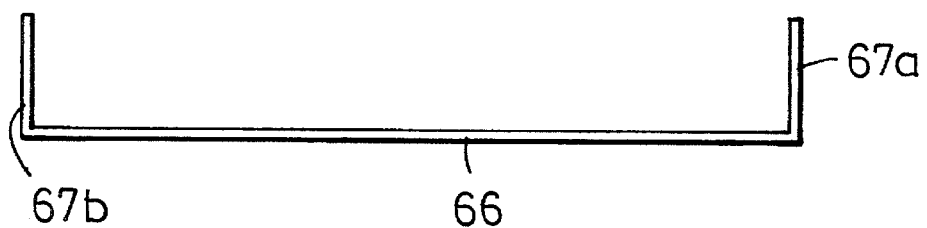
FIG. 25B is a fragmentary plan view of the rotary shaft of FIG. 25A.
Figure 26:
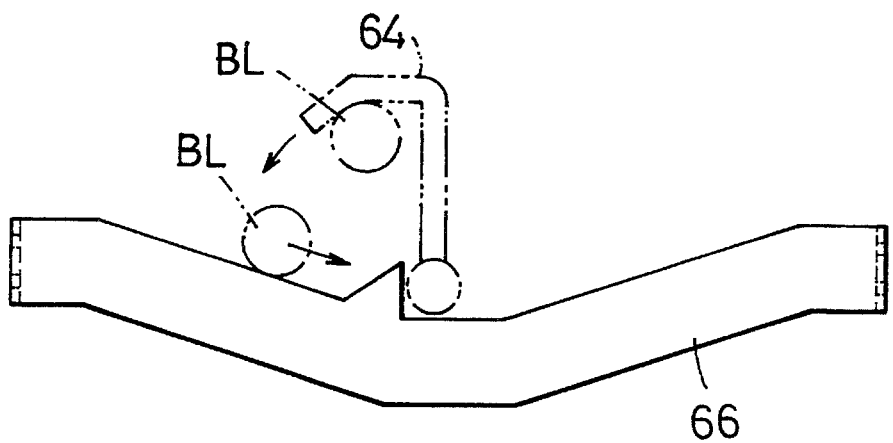
FIG. 26 is a side view of another aspect of the rotary shaft.

In addition, various design modifications can be made in the present invention. For example, the coarse crushing blades 64 may be provided in a flat plate shape, as shown in FIGS. 24A and 24B, while their tip end parts are bent onto one side and their space in axial direction of the shaft 61 is gradually expanded as separated from the shaft, so that any shorter garbage stuff in the mixture may be caught at a position closer to the shaft for its effective crushing. This is for the reason that, in the case of the foregoing embodiments, the mixture stuff BL is caused to show a tendency of rotating about the rotary shaft as shown by arrows in FIG. 26, but such rotation can be prevented by the arrangement of FIGS. 24A and 24B. Further, the stationary blade 66 cooperating with the coarse crushing blades 64 may be formed to have notches at central portion in both side edges and extending mutually oppositely, as shown in FIGS. 25A to 25C, for improving the crushing action with respect to the mixture being treated.

What is claimed is:

1. A garbage treating apparatus, comprising:
   a treating vessel for receiving garbage for fermentative composition;
   an agent adding mechanism arranged for adding to garbage in the vessel a fermentative garbage decomposing agent carrying a microparasite which promotes fermentative decomposition;
   a load circuit including a first mechanism operable for circulating air into and out of the vessel at an adjustable circulation rate, a second mechanism operable for heating the circulated air to an adjustable air temperature level, and a third mechanism operable for stirring the garbage and the decomposing agent at an adjustable stirring frequency level to form a mixture thereof within the vessel;
   a sensing mechanism operable for sensing a moisture content of the mixture in the vessel; and
   a control mechanism connected to the sensing mechanism and the load circuit and operable for comparing a sensed moisture content with a reference value and for establishing a high moisture evaporation mode of operation of the load circuit such that respective ones of the first, second, and third mechanisms operate to establish a relatively high rate, temperature, and frequency, respectively, in response to the sensed moisture content being above the reference value, and for establishing a low moisture evaporation mode of operation of the load circuit wherein respective ones of the first, second and third mechanisms continue to operate, however to establish a relatively lower rate, temperature, and frequency, respectively, in response to the sensed moisture content being below the reference value.

2. The apparatus according to claim 1 wherein said high evaporation mode is changed over to said low evaporation mode after a continued operation for a shorter period than a cycle in which the garbage is thrown in the apparatus.

3. The apparatus according to claim 2 wherein said low evaporation mode further includes a weak treating mode and a weaker treating mode.

4. The apparatus according to claim 1 wherein said high evaporation mode includes a normal treating mode and a strong treating mode, and said low evaporating mode includes a weak treating mode and a weakest treating mode.

5. The apparatus according to claim 4 which further comprises means for providing an alarm when one of said strong, weak and weakest treating modes continues for a fixed period.

6. The apparatus accoridng to claim 4 which further comprises a rising-drive means for executing said strong treating mode upon starting of the treatment, and means for starting said rising-drive means.

7. The apparatus according to claim 1 wherein said control mechanism includes a moisture content determining means for obtaining an average of a plurality of values of said moisture content obtained by said moisture content sensing mechanism.

8. The apparatus according to claim 7 wherein said moisture content determining means determines the moisture content when values different from a predetermined moisture content value are detected for a plurality of times.

9. The apparatus according to claim 1 which further comprises means for correcting any fluctuation in outputs of said moisture content sensing mechanism.

10. The apparatus according to claim 1 wherein said sensing mechanism comprises a negative characteristic thermistor.

* * * * *